US012765961B2

(12) United States Patent
Rockrohr

(10) Patent No.: US 12,765,961 B2
(45) Date of Patent: Oct. 20, 2026

(54) SYSTEM AND METHOD FOR SURGICAL INSTRUMENT USE PREDICTION

(71) Applicant: Covidien LP, Mansfield, MA (US)

(72) Inventor: Brian A. Rockrohr, Guilford, CT (US)

(73) Assignee: Covidien LP, Mansfield, MA (US)

( * ) Notice: Subject to any disclaimer, the term of this patent is extended or adjusted under 35 U.S.C. 154(b) by 229 days.

(21) Appl. No.: 18/576,145

(22) PCT Filed: Jul. 26, 2022

(86) PCT No.: PCT/IB2022/056857
§ 371 (c)(1),
(2) Date: Jan. 3, 2024

(87) PCT Pub. No.: WO2023/012574
PCT Pub. Date: Feb. 9, 2023

(65) Prior Publication Data

US 2024/0315795 A1 Sep. 26, 2024

Related U.S. Application Data

(60) Provisional application No. 63/228,656, filed on Aug. 3, 2021.

(51) Int. Cl.

| | |
|---|---|
| ***A61B 34/30*** | (2016.01) |
| ***A61B 17/00*** | (2006.01) |
| ***A61B 34/00*** | (2016.01) |
| ***A61B 34/37*** | (2016.01) |
| ***A61B 90/00*** | (2016.01) |
| ***G16H 40/40*** | (2018.01) |

(52) U.S. Cl.
CPC .............. *A61B 90/08* (2016.02); *A61B 17/00* (2013.01); *A61B 34/25* (2016.02); *A61B 34/37* (2016.02); *G16H 40/40* (2018.01); *A61B 2017/00123* (2013.01); *A61B 2090/0803* (2016.02)

(58) Field of Classification Search
CPC ......... A61B 34/30; A61B 34/35; A61B 34/37; A61B 2090/0803; G16H 40/40
See application file for complete search history.

(56) References Cited

U.S. PATENT DOCUMENTS

| | | | | |
|---|---|---|---|---|
| 5,391,081 | A * | 2/1995 | Lampotang ............ | G09B 23/28 434/262 |
| 6,066,163 | A * | 5/2000 | John ...................... | G16H 20/40 607/45 |
| 6,132,368 | A | 10/2000 | Cooper | |
| 6,206,903 | B1 | 3/2001 | Ramans | |
| 6,246,200 | B1 | 6/2001 | Blumenkranz et al. | |
| 6,312,435 | B1 | 11/2001 | Wallace et al. | |

(Continued)

OTHER PUBLICATIONS

International Search Report and Written Opinion of the International Searching Authority issued in corresponding application PCT/IB2022/056857 mailed Dec. 5, 2022 (8 pages).

*Primary Examiner* — Eric D. Bertram
(74) *Attorney, Agent, or Firm* — Carter, DeLuca & Farrell, LLP

(57) ABSTRACT

A surgical robotic system includes a controller configured to access usage data pertaining to a surgical instrument and to estimate a predicted number of uses remaining for the surgical instrument. The controller is further configured to enable or disable the surgical instrument based on the predicted number of uses remaining.

12 Claims, 7 Drawing Sheets

(56) References Cited

U.S. PATENT DOCUMENTS 6,331,181 B1 12/2001 Tierney et al.
6,394,998 B1 5/2002 Wallace et al.
6,424,885 B1 7/2002 Niemeyer et al.
6,441,577 B2 8/2002 Blumenkranz et al.
6,459,926 B1 10/2002 Nowlin et al.
6,491,691 B1 12/2002 Morley et al.
6,491,701 B2 12/2002 Tierney et al.
6,493,608 B1 12/2002 Niemeyer
6,565,554 B1 5/2003 Niemeyer
6,645,196 B1 11/2003 Nixon et al.
6,659,939 B2 12/2003 Moll et al.
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco et al.
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez et al.
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank

(56) References Cited

U.S. PATENT DOCUMENTS

| | | | |
|---|---|---|---|
| 8,858,547 B2 | 10/2014 | Brogna | |
| 8,862,268 B2 | 10/2014 | Robinson et al. | |
| 8,864,751 B2 | 10/2014 | Prisco et al. | |
| 8,864,752 B2 | 10/2014 | Diolaiti et al. | |
| 8,903,546 B2 | 12/2014 | Diolaiti et al. | |
| 8,903,549 B2 | 12/2014 | Itkowitz et al. | |
| 8,911,428 B2 | 12/2014 | Cooper et al. | |
| 8,912,746 B2 | 12/2014 | Reid et al. | |
| 8,944,070 B2 | 2/2015 | Guthart et al. | |
| 8,989,903 B2 | 3/2015 | Weir et al. | |
| 9,002,518 B2 | 4/2015 | Manzo et al. | |
| 9,014,856 B2 | 4/2015 | Manzo et al. | |
| 9,016,540 B2 | 4/2015 | Whitman et al. | |
| 9,019,345 B2 | 4/2015 | O'Grady et al. | |
| 9,043,027 B2 | 5/2015 | Durant et al. | |
| 9,050,120 B2 | 6/2015 | Swarup et al. | |
| 9,055,961 B2 | 6/2015 | Manzo et al. | |
| 9,068,628 B2 | 6/2015 | Solomon et al. | |
| 9,078,684 B2 | 7/2015 | Williams | |
| 9,084,623 B2 | 7/2015 | Gomez et al. | |
| 9,095,362 B2 | 8/2015 | Dachs, II et al. | |
| 9,096,033 B2 | 8/2015 | Holop et al. | |
| 9,101,381 B2 | 8/2015 | Burbank et al. | |
| 9,113,877 B1 | 8/2015 | Whitman et al. | |
| 9,138,284 B2 | 9/2015 | Krom et al. | |
| 9,144,456 B2 | 9/2015 | Rosa et al. | |
| 9,198,730 B2 | 12/2015 | Prisco et al. | |
| 9,204,923 B2 | 12/2015 | Manzo et al. | |
| 9,226,648 B2 | 1/2016 | Saadat et al. | |
| 9,226,750 B2 | 1/2016 | Weir et al. | |
| 9,226,761 B2 | 1/2016 | Burbank | |
| 9,232,984 B2 | 1/2016 | Guthart et al. | |
| 9,241,766 B2 | 1/2016 | Duque et al. | |
| 9,241,767 B2 | 1/2016 | Prisco et al. | |
| 9,241,769 B2 | 1/2016 | Larkin et al. | |
| 9,247,996 B1 * | 2/2016 | Merana | A61B 90/94 |
| 9,259,275 B2 | 2/2016 | Burbank | |
| 9,259,277 B2 | 2/2016 | Rogers et al. | |
| 9,259,281 B2 | 2/2016 | Griffiths et al. | |
| 9,259,282 B2 | 2/2016 | Azizian et al. | |
| 9,261,172 B2 | 2/2016 | Solomon et al. | |
| 9,265,567 B2 | 2/2016 | Orban, III et al. | |
| 9,265,584 B2 | 2/2016 | Itkowitz et al. | |
| 9,283,049 B2 | 3/2016 | Diolaiti et al. | |
| 9,301,811 B2 | 4/2016 | Goldberg et al. | |
| 9,314,307 B2 | 4/2016 | Richmond et al. | |
| 9,317,651 B2 | 4/2016 | Nixon | |
| 9,345,546 B2 | 5/2016 | Toth et al. | |
| 9,393,017 B2 | 7/2016 | Flanagan et al. | |
| 9,402,689 B2 | 8/2016 | Prisco et al. | |
| 9,417,621 B2 | 8/2016 | Diolaiti et al. | |
| 9,424,303 B2 | 8/2016 | Hoffman et al. | |
| 9,433,418 B2 | 9/2016 | Whitman et al. | |
| 9,446,517 B2 | 9/2016 | Burns et al. | |
| 9,452,020 B2 | 9/2016 | Griffiths et al. | |
| 9,474,569 B2 | 10/2016 | Manzo et al. | |
| 9,480,533 B2 | 11/2016 | Devengenzo et al. | |
| 9,503,713 B2 | 11/2016 | Zhao et al. | |
| 9,550,300 B2 | 1/2017 | Danitz et al. | |
| 9,554,859 B2 | 1/2017 | Nowlin et al. | |
| 9,566,124 B2 | 2/2017 | Prisco et al. | |
| 9,579,164 B2 | 2/2017 | Itkowitz et al. | |
| 9,585,641 B2 | 3/2017 | Cooper et al. | |
| 9,615,883 B2 | 4/2017 | Schena et al. | |
| 9,623,563 B2 | 4/2017 | Nixon | |
| 9,623,902 B2 | 4/2017 | Griffiths et al. | |
| 9,629,520 B2 | 4/2017 | Diolaiti | |
| 9,662,177 B2 | 5/2017 | Weir et al. | |
| 9,664,262 B2 | 5/2017 | Donlon et al. | |
| 9,675,354 B2 | 6/2017 | Weir et al. | |
| 9,687,312 B2 | 6/2017 | Dachs, II et al. | |
| 9,700,334 B2 | 7/2017 | Hinman et al. | |
| 9,718,190 B2 | 8/2017 | Larkin et al. | |
| 9,730,719 B2 | 8/2017 | Brisson et al. | |
| 9,737,199 B2 | 8/2017 | Pistor et al. | |
| 9,795,446 B2 | 10/2017 | DiMaio et al. | |
| 9,797,484 B2 | 10/2017 | Solomon et al. | |
| 9,801,690 B2 | 10/2017 | Larkin et al. | |
| 9,814,530 B2 | 11/2017 | Weir et al. | |
| 9,814,536 B2 | 11/2017 | Goldberg et al. | |
| 9,814,537 B2 | 11/2017 | Itkowitz et al. | |
| 9,820,823 B2 | 11/2017 | Richmond et al. | |
| 9,827,059 B2 | 11/2017 | Robinson et al. | |
| 9,830,371 B2 | 11/2017 | Hoffman et al. | |
| 9,839,481 B2 | 12/2017 | Blumenkranz et al. | |
| 9,839,487 B2 | 12/2017 | Dachs, II | |
| 9,850,994 B2 | 12/2017 | Schena | |
| 9,855,102 B2 | 1/2018 | Blumenkranz | |
| 9,855,107 B2 | 1/2018 | Labonville et al. | |
| 9,872,737 B2 | 1/2018 | Nixon | |
| 9,877,718 B2 | 1/2018 | Weir et al. | |
| 9,883,920 B2 | 2/2018 | Blumenkranz | |
| 9,888,974 B2 | 2/2018 | Niemeyer | |
| 9,895,813 B2 | 2/2018 | Blumenkranz et al. | |
| 9,901,408 B2 | 2/2018 | Larkin | |
| 9,918,800 B2 | 3/2018 | Itkowitz et al. | |
| 9,943,375 B2 | 4/2018 | Blumenkranz et al. | |
| 9,948,852 B2 | 4/2018 | Lilagan et al. | |
| 9,949,798 B2 | 4/2018 | Weir | |
| 9,949,802 B2 | 4/2018 | Cooper | |
| 9,952,107 B2 | 4/2018 | Blumenkranz et al. | |
| 9,956,044 B2 | 5/2018 | Gomez et al. | |
| 9,980,778 B2 | 5/2018 | Ohline et al. | |
| 10,008,017 B2 | 6/2018 | Itkowitz et al. | |
| 10,028,793 B2 | 7/2018 | Griffiths et al. | |
| 10,033,308 B2 | 7/2018 | Chaghajerdi et al. | |
| 10,034,719 B2 | 7/2018 | Richmond et al. | |
| 10,052,167 B2 | 8/2018 | Au et al. | |
| 10,085,811 B2 | 10/2018 | Weir et al. | |
| 10,092,165 B2 | 10/2018 | Power | |
| 10,092,344 B2 | 10/2018 | Mohr et al. | |
| 10,123,844 B2 | 11/2018 | Nowlin et al. | |
| 10,175,096 B2 | 1/2019 | Dickerson | |
| 10,188,471 B2 | 1/2019 | Brisson | |
| 10,201,390 B2 | 2/2019 | Swarup et al. | |
| 10,213,202 B2 | 2/2019 | Flanagan et al. | |
| 10,258,416 B2 | 4/2019 | Mintz et al. | |
| 10,278,782 B2 | 5/2019 | Jarc et al. | |
| 10,278,783 B2 | 5/2019 | Itkowitz et al. | |
| 10,282,881 B2 | 5/2019 | Itkowitz et al. | |
| 10,335,242 B2 | 7/2019 | Devengenzo et al. | |
| 10,405,934 B2 | 9/2019 | Prisco et al. | |
| 10,433,922 B2 | 10/2019 | Itkowitz et al. | |
| 10,464,219 B2 | 11/2019 | Robinson et al. | |
| 10,485,621 B2 | 11/2019 | Morrissette et al. | |
| 10,500,004 B2 | 12/2019 | Hanuschik et al. | |
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald, II | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 10,939,969 B2 | 3/2021 | Swarup et al. | |
| 10,939,973 B2 | 3/2021 | DiMaio et al. | |
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |
| 10,973,519 B2 | 4/2021 | Weir et al. | |
| 10,984,567 B2 | 4/2021 | Itkowitz et al. | |

(56) References Cited

U.S. PATENT DOCUMENTS

| | | | | |
|---|---|---|---|---|
| 10,993,773 | B2 | 5/2021 | Cooper et al. | |
| 10,993,775 | B2 | 5/2021 | Cooper et al. | |
| 11,000,331 | B2 | 5/2021 | Krom et al. | |
| 11,013,567 | B2 | 5/2021 | Wu et al. | |
| 11,020,138 | B2 | 6/2021 | Ragosta | |
| 11,020,191 | B2 | 6/2021 | Diolaiti et al. | |
| 11,020,193 | B2 | 6/2021 | Wixey et al. | |
| 11,026,755 | B2 | 6/2021 | Weir et al. | |
| 11,026,759 | B2 | 6/2021 | Donlon et al. | |
| 11,040,189 | B2 | 6/2021 | Vaders et al. | |
| 11,045,077 | B2 | 6/2021 | Stern et al. | |
| 11,045,274 | B2 | 6/2021 | Dachs, II et al. | |
| 11,058,501 | B2 | 7/2021 | Tokarchuk et al. | |
| 11,076,925 | B2 | 8/2021 | DiMaio et al. | |
| 11,090,119 | B2 | 8/2021 | Burbank | |
| 11,096,687 | B2 | 8/2021 | Flanagan et al. | |
| 11,098,803 | B2 | 8/2021 | Duque et al. | |
| 11,109,925 | B2 | 9/2021 | Cooper et al. | |
| 11,116,578 | B2 | 9/2021 | Hoffman et al. | |
| 11,129,683 | B2 | 9/2021 | Steger et al. | |
| 11,135,029 | B2 | 10/2021 | Suresh et al. | |
| 11,147,552 | B2 | 10/2021 | Burbank et al. | |
| 11,147,640 | B2 | 10/2021 | Jarc et al. | |
| 11,154,373 | B2 | 10/2021 | Abbott et al. | |
| 11,154,374 | B2 | 10/2021 | Hanuschik et al. | |
| 11,160,622 | B2 | 11/2021 | Goldberg et al. | |
| 11,160,625 | B2 | 11/2021 | Wixey et al. | |
| 11,161,243 | B2 | 11/2021 | Rabindran et al. | |
| 11,166,758 | B2 | 11/2021 | Mohr et al. | |
| 11,166,770 | B2 | 11/2021 | DiMaio et al. | |
| 11,166,773 | B2 | 11/2021 | Ragosta et al. | |
| 11,173,597 | B2 | 11/2021 | Rabindran et al. | |
| 11,185,378 | B2 | 11/2021 | Weir et al. | |
| 11,191,596 | B2 | 12/2021 | Thompson et al. | |
| 11,197,729 | B2 | 12/2021 | Thompson et al. | |
| 11,213,360 | B2 | 1/2022 | Hourtash et al. | |
| 11,221,863 | B2 | 1/2022 | Azizian et al. | |
| 11,234,700 | B2 | 2/2022 | Ragosta et al. | |
| 11,241,274 | B2 | 2/2022 | Vaders et al. | |
| 11,241,290 | B2 | 2/2022 | Waterbury et al. | |
| 11,259,870 | B2 | 3/2022 | DiMaio et al. | |
| 11,259,884 | B2 | 3/2022 | Burbank | |
| 11,272,993 | B2 | 3/2022 | Gomez et al. | |
| 11,272,994 | B2 | 3/2022 | Saraliev et al. | |
| 11,291,442 | B2 | 4/2022 | Wixey et al. | |
| 11,291,513 | B2 | 4/2022 | Manzo et al. | |
| 11,344,378 | B2 * | 5/2022 | Alden .................... | A61B 34/30 |
| 11,376,002 | B2 | 7/2022 | Shelton, IV et al. | |
| 11,376,098 | B2 | 7/2022 | Shelton, IV et al. | |
| 11,381,759 | B2 | 7/2022 | Zhao et al. | |
| 11,382,621 | B2 | 7/2022 | Scheib et al. | |
| 11,382,624 | B2 | 7/2022 | Harris et al. | |
| 11,382,625 | B2 | 7/2022 | Huitema et al. | |
| 11,382,626 | B2 | 7/2022 | Shelton, IV et al. | |
| 11,382,627 | B2 | 7/2022 | Huitema et al. | |
| 11,382,638 | B2 | 7/2022 | Harris et al. | |
| 11,382,644 | B2 | 7/2022 | Schoettgen et al. | |
| 11,389,160 | B2 | 7/2022 | Shelton, IV et al. | |
| 11,389,255 | B2 | 7/2022 | DiMaio et al. | |
| 11,399,906 | B2 | 8/2022 | Shelton, IV et al. | |
| 11,406,379 | B2 | 8/2022 | Hess et al. | |
| 11,410,259 | B2 | 8/2022 | Harris et al. | |
| 11,419,630 | B2 | 8/2022 | Yates et al. | |
| 11,424,027 | B2 | 8/2022 | Shelton, IV | |
| 11,432,888 | B2 | 9/2022 | Diolaiti et al. | |
| 11,432,893 | B2 | 9/2022 | Itkowitz et al. | |
| 11,432,895 | B2 | 9/2022 | Loh et al. | |
| 11,439,390 | B2 | 9/2022 | Patel et al. | |
| 11,439,391 | B2 | 9/2022 | Bruns et al. | |
| 11,468,791 | B2 | 10/2022 | Jarc et al. | |
| 11,471,155 | B2 | 10/2022 | Shelton, IV et al. | |
| 11,471,221 | B2 | 10/2022 | Zhao et al. | |
| 11,478,308 | B2 | 10/2022 | Hoffman et al. | |
| 11,490,977 | B2 | 11/2022 | Schena et al. | |
| 11,497,499 | B2 | 11/2022 | Shelton, IV et al. | |
| 11,504,119 | B2 | 11/2022 | Shelton, IV et al. | |
| 11,504,124 | B2 | 11/2022 | Patel et al. | |
| 11,510,743 | B2 | 11/2022 | Shelton, IV et al. | |
| 11,517,312 | B2 | 12/2022 | Wixey | |
| 11,517,325 | B2 | 12/2022 | Shelton, IV et al. | |
| 11,518,048 | B2 | 12/2022 | Saraliev et al. | |
| 12,029,512 | B2 * | 7/2024 | Rosa ...................... | A61B 34/25 |
| 12,186,548 | B2 * | 1/2025 | Jackson ............. | A61N 1/36034 |
| 2007/0156285 | A1 * | 7/2007 | Sillman .................. | A61B 34/70 700/251 |
| 2008/0208287 | A1 * | 8/2008 | Palermo ................. | A61N 1/323 607/3 |
| 2008/0249430 | A1 * | 10/2008 | John ...................... | A61B 5/372 600/544 |
| 2010/0152807 | A1 * | 6/2010 | Grill .................... | A61N 1/3615 607/45 |
| 2014/0142410 | A1 * | 5/2014 | Erb ........................ | A61B 5/383 600/383 |
| 2014/0163627 | A1 * | 6/2014 | Starr ................... | A61M 5/1723 607/45 |
| 2015/0297200 | A1 * | 10/2015 | Fitzsimmons ... | A61B 17/07207 606/1 |
| 2017/0212995 | A1 * | 7/2017 | Ingmanson ............ | G16H 40/20 |
| 2017/0333073 | A1 * | 11/2017 | Faller ............. | A61B 17/320092 |
| 2017/0360520 | A1 | 12/2017 | Hares | |
| 2018/0140843 | A1 * | 5/2018 | Kent ...................... | A61N 1/025 |
| 2018/0353759 | A1 * | 12/2018 | Starr ........................ | A61B 5/37 |
| 2019/0143113 | A1 * | 5/2019 | Wong ................. | A61N 1/36031 607/48 |
| 2019/0206565 | A1 * | 7/2019 | Shelton, IV ........... | A61B 90/90 |
| 2019/0223850 | A1 * | 7/2019 | Fitzsimmons ... | A61B 17/07207 |
| 2020/0061378 | A1 * | 2/2020 | Ganguly ............ | A61N 1/36031 |
| 2020/0345437 | A1 * | 11/2020 | Rosa ...................... | A61B 90/08 |
| 2021/0402172 | A1 * | 12/2021 | Ross .................... | A61B 5/1101 |

* cited by examiner

SYSTEM AND METHOD FOR SURGICAL INSTRUMENT USE PREDICTION

The present application is a U.S. National Stage Application filed under 35 U.S.C. § 371 (a) of International Patent Application No. PCT/IB2022/056857, filed on Jul. 26, 2022, which claims the benefit of and priority to U.S. Patent Provisional Application No. 63/228,656, filed on Aug. 3, 2021. The entire disclosures of the foregoing applications are incorporated by reference herein.

BACKGROUND

Technical Field

The present disclosure generally relates to surgical instruments and in particular, to tracking use of the surgical instrument and predicting a number of remaining uses based on prior use patterns.

Background of Related Art

Surgical robotic systems are currently being used in minimally invasive medical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

Surgical instruments used with robotic systems have a finite life due to wear and tear imparted on surgical instruments' components. Thus, there is a need for a system and a method to track and predict instrument use to prevent using the surgical instruments beyond their preset lifetimes.

SUMMARY

According to one aspect of the present disclosure, a surgical robotic system is disclosed, which includes a robotic arm; a surgical instrument configured to couple to the robotic arm, and a controller configured to: access usage data pertaining the surgical instrument; calculate a predicted number of uses remaining for the surgical instrument; and disable the surgical instrument based on the predicted number of uses.

Implementations of the above embodiment may include one or more of the following features. According to one aspect of the above embodiment, the usage data may include maximum life data and previous use data. The maximum life data may include a number of maximum uses and a maximum use time. The previous use data may include a number of previous uses, a previous use time, and an expired flag. The controller may be further configured to disable the surgical instrument based on the expired flag being set to true. The controller may be further configured to disable the surgical instrument based on the previous use time exceeding the maximum use time. The controller may be further configured to disable the surgical instrument based on the number of previous uses exceeding the number of maximum uses. The controller may be further configured to calculate an average use time based on the previous use time and the number of previous uses. The controller may be further configured to calculate the predicted number of uses based on the maximum use time and the average use time. The surgical robotic system may further include a display configured to output a graphical user interface may including a usage indicator status pertaining the surgical instrument. The surgical instrument may also include a storage device configured to store the usage data. The controller may be further configured to update the usage data following the use of the surgical instrument.

According to another aspect of the present disclosure, a method for controlling a surgical system is disclosed and includes accessing usage data pertaining to a surgical instrument; calculating a predicted number of uses remaining for the surgical instrument, and disabling the surgical instrument based on the predicted number of uses.

Implementations of the above embodiment may include one or more of the following features. According to one aspect of the above embodiment, accessing the usage data may include accessing maximum life data and previous use data. Accessing the maximum life data may include accessing a number of maximum uses and a maximum use time. Accessing the previous use data may include accessing a number of previous uses, a previous use time, and an expired flag. Calculating the predicted number of uses further may include calculating an average use time based on the previous use time and the number of previous uses. Calculating the predicted number of uses is based on the maximum use time and the average use time. The method may also include displaying on a graphical user interface a usage indicator status pertaining the surgical instrument. The method may also include updating the usage data following the use of the surgical instrument.

BRIEF DESCRIPTION OF THE DRAWINGS

Various aspects of the present disclosure are described herein with reference to the drawings wherein.

DETAILED DESCRIPTION

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgeon console, a control tower, and one or more movable carts having a surgical robotic arm coupled to a setup arm. The surgeon console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

Figure 1:
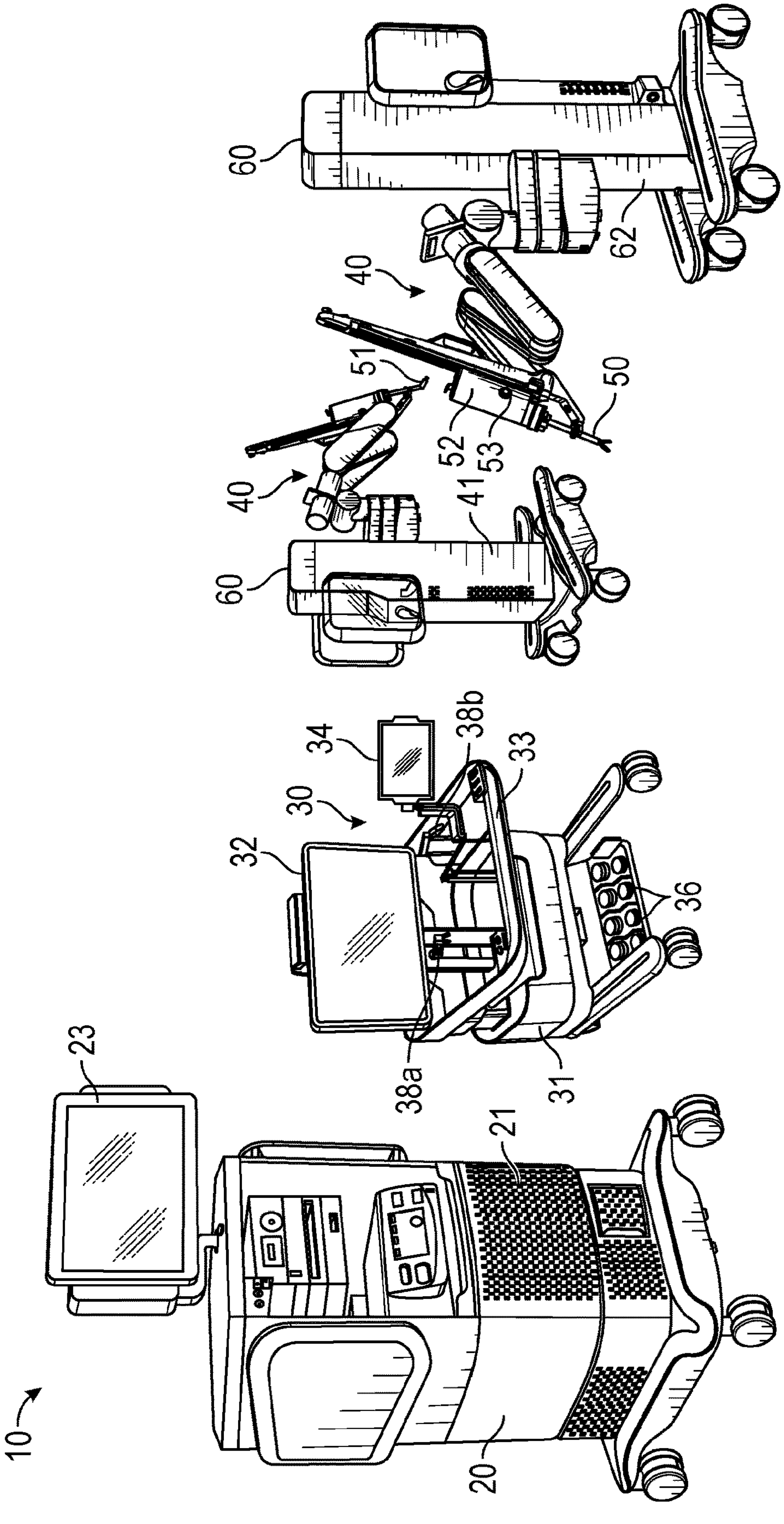
FIG. 1 is a schematic illustration of a surgical robotic system including a control tower, a console, and one or more surgical robotic arms each disposed on a movable cart according to an aspect of the present disclosure.

With reference to FIG. 1, a surgical robotic system 10 includes a control tower 20, which is connected to all of the components of the surgical robotic system 10 including a surgeon console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In aspects, the surgical instrument 50 may be configured for open surgical procedures. In aspects, the surgical instrument 50 may be an endoscope, such as an endoscopic camera 51, configured to provide a video feed for the user. In further aspects, the surgical instrument 50 may be an electrosurgical forceps configured to seal tissue by compressing tissue between jaw members and applying electrosurgical current thereto. In yet further aspects, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 perform the image processing based on the depth estimating algorithms of the present disclosure and output the processed video stream.

The surgeon console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs. The video processing device 56 is configured to process the video feed from the endoscopic camera 51 and to output a processed video stream on the first displays 32 of the surgeon console 30 and/or the display 23 of the control tower 20.

The surgeon console 30 also includes a plurality of user interface devices, such as foot pedals 36 and a pair of handle controllers 38*a* and 38*b* which are used by a user to remotely control robotic arms 40. The surgeon console further includes an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38*a* and 38*b*.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
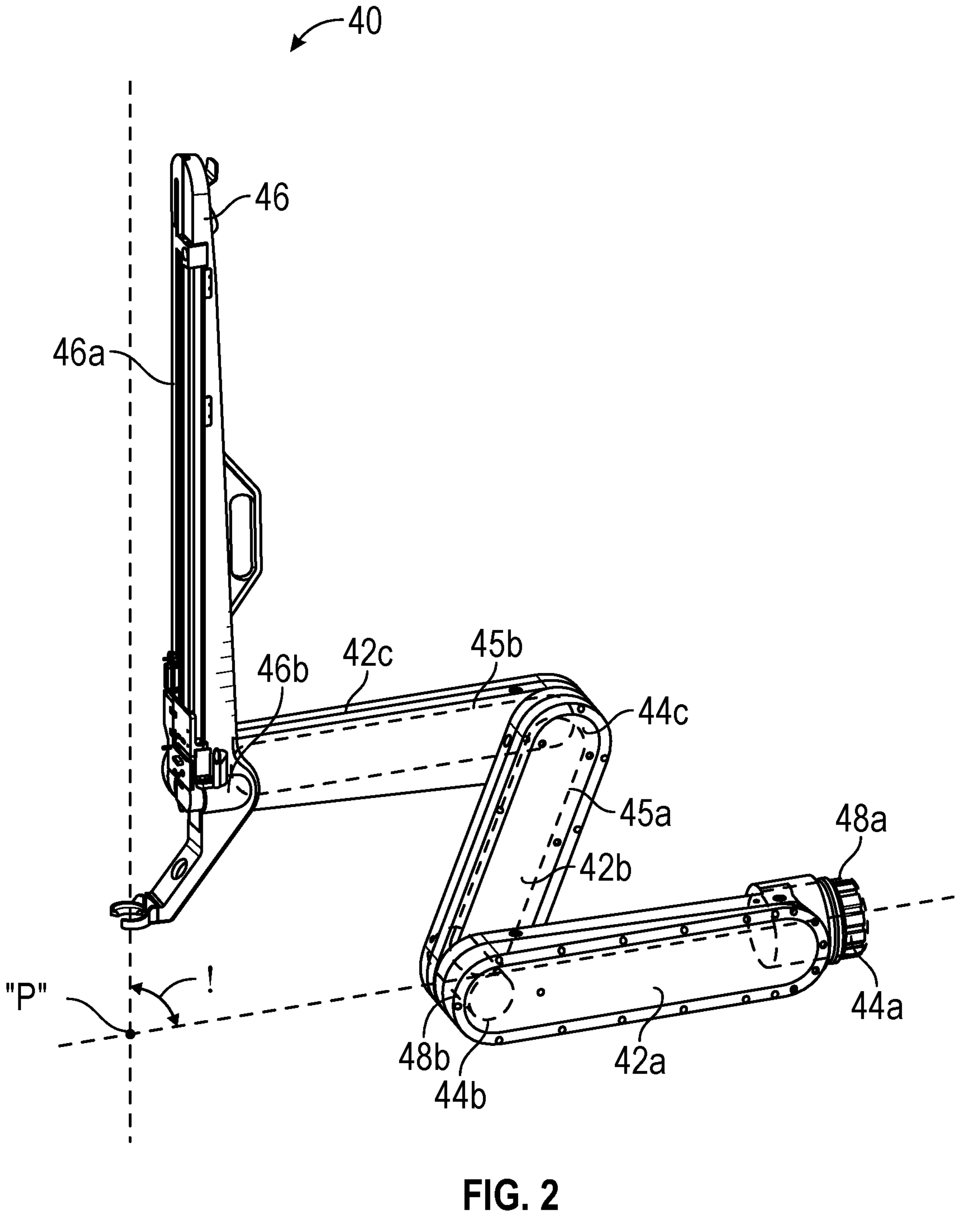
FIG. 2 is a perspective view of a surgical robotic arm of the surgical robotic system of FIG. 1 according to an aspect of the present disclosure.
Figure 3:
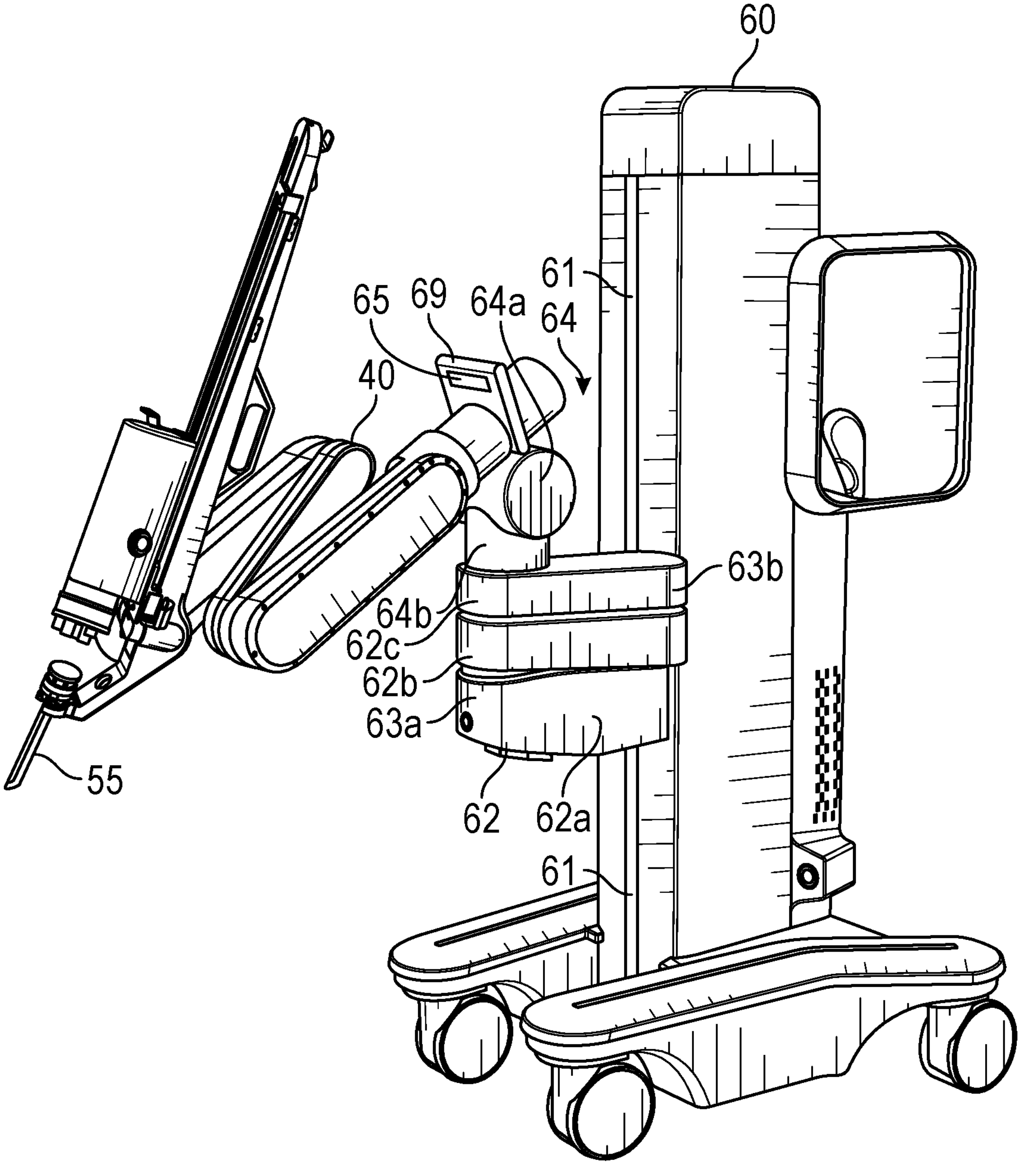
FIG. 3 is a perspective view of a setup arm with the surgical robotic arm of the surgical robotic system of FIG. 1 according to an aspect of the present disclosure.

With reference to FIG. 2, each of the robotic arms 40 may include a plurality of links 42*a*, 42*b*, 42*c*, which are interconnected at joints 44*a*, 44*b*, 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In aspects, the robotic arm 40 may be coupled to a surgical table. The setup arm 62 includes controls 65 for adjusting movement of the links 62*a*, 62*b*, 62*c* as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*c* via the belt 45*b*. Joint 44*c* may include a transfer case coupling the belts 45*a* and 45*b*, such that the actuator 48*b* is configured to rotate each of the links 42*b*, 42*c* and the holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In aspects, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic port 55 (FIG. 3) held by the holder 46.

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

Figure 4:
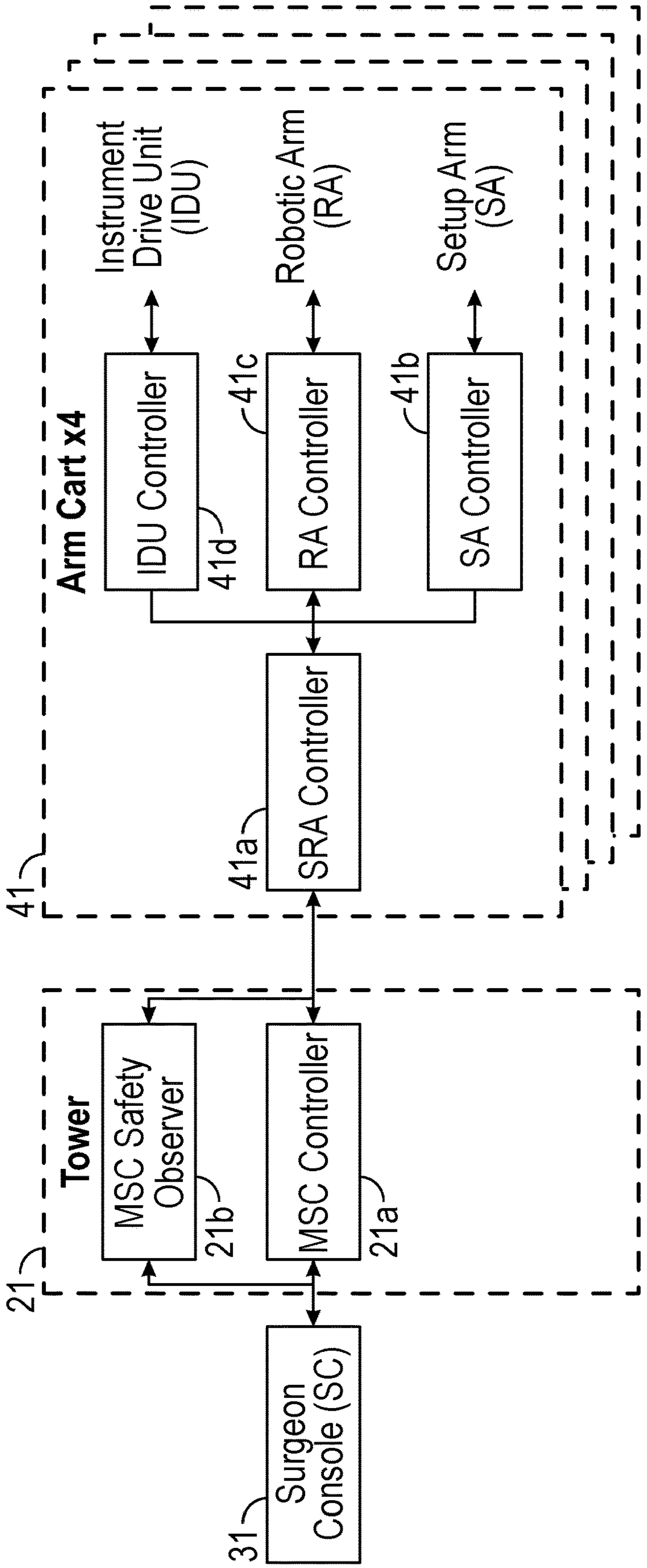
FIG. 4 is a schematic diagram of a computer architecture of the surgical robotic system of FIG. 1 according to an aspect of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgeon console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgeon console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

The setup arm controller 41*b* controls each of joints 63*a* and 63*b*, and the rotatable base 64 of the setup arm 62 and calculates desired motor movement commands (e.g., motor torque) for the pitch axis and controls the brakes. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the handle controller controlling the robotic arm 40, e.g., the handle controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controller 38*a* may be embodied as a coordinate position and role-pitch-yaw ("RPY") orientation relative to a coordinate reference frame, which is fixed to the surgeon console 30. The desired pose of the instrument 50 is relative to a fixed frame on the robotic arm 40. The pose of the handle controller 38*a* is then scaled by a scaling function executed by the controller 21*a*. In aspects, the coordinate position is scaled down and the orientation is scaled up by the scaling function. In addition, the controller 21*a* also executes a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
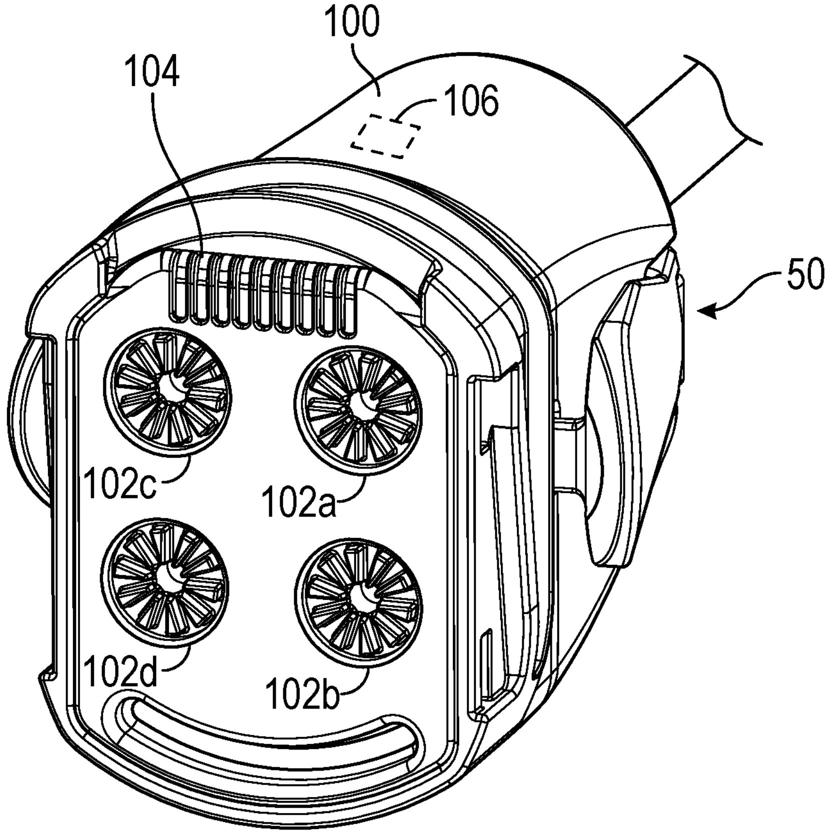
FIG. 5 is a rear perspective view of a surgical instrument.

With reference to FIG. 5, the instrument 50 includes a housing assembly 100 enclosing drive couplers 102*a-d* configured for selective connection to the IDU 52. The IDU 52 includes a plurality of motors configured to actuate each of the drive couplers 102*a-d* thereby actuating the instrument 50. The housing assembly 100 also includes an electrical connector 104 configured for selective connection to the IDU 52. The instrument 50 may include electronics, including, and not limited to, a memory 106, wired or wireless communication circuitry for receiving and transmitting data or information. The IDU 52 may be configured to permit passage or routing of a dedicated electrocautery cable or the like for use and connection to an electrosurgical based electromechanical surgical instrument (e.g., for ablation, coagulation, sealing, etc.).

The memory 106 may be any suitable storage device, such as flash memory and is configured to store identification information of the instrument 50, usage data, and the like. The memory 106 may be accessed by any controllers of the surgical robotic system 10, which may be the computers 21, 31, 41. In an exemplary embodiment, the main controller 21*a* is configured to read and write to the memory 106 including retrieving and updating usage data. The computers 21, 31, 41 are configured to communicate with the memory 106 through the electrical connector 104 and/or any other wired or wireless interface.

Usage data may be stored in any suitable data structure and includes actual time used, which may be measured in seconds, minutes, etc., number of uses. The main controller 21*a* uses the usage data to calculate remaining life of the instrument 50 and displays the remaining life on any of the displays 23, 32, and/or 34.

Figure 6:
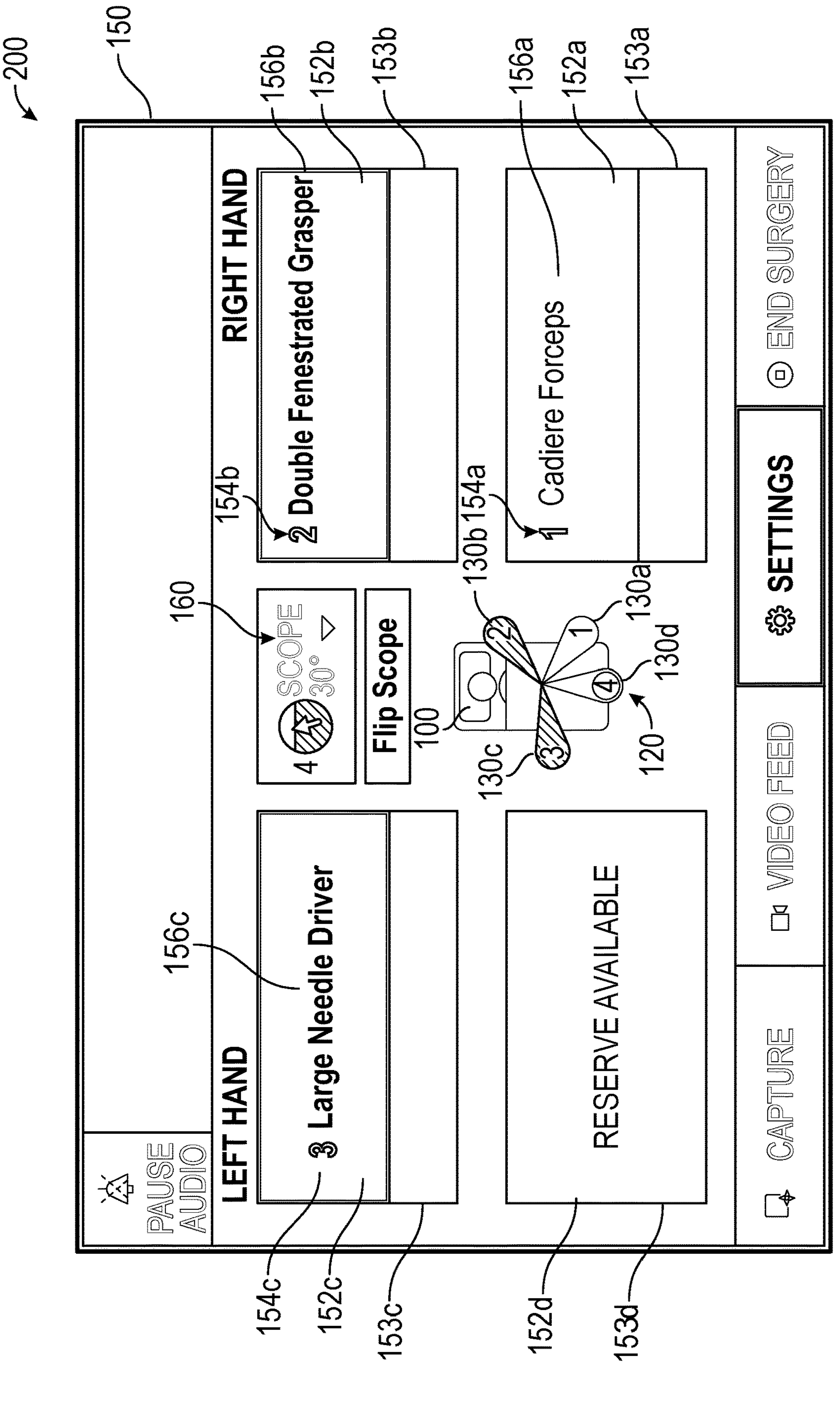
FIG. 6 is a graphical user interface displayed on a display of the surgical robotic system of FIG. 1 according to an embodiment of the present disclosure.

As shown in an exemplary display 200 of FIG. 6. The display 200 may be any of the displays 23, 32, and 34 shows a graphical user interface 150, which includes a plurality of regions 153*a-d* having graphical representations 152*a-c* for each of the three robotic arms 40, which are numbered "1"-"3" and a reserve graphical representation 152*d*. Each of the graphical representations 152*a-c* includes an identification number 154*a-c* and an instrument type 156*a-c*. The user interface 150 also includes an orientation indicator 160. The orientation indicator 160, which shows rotation and pitch indication of the camera 51, which shows rotation and pitch indication of the camera 51 that is coupled to the robotic arm 40*d* numbered "4".

The controller 21*a* calculates remaining instrument life for the instrument 50 based on previous use of the instrument 50. Rather than outputting a percentage of total minutes used vs. the total minutes allowed for the instrument 50, which does not provide any context for how many actual uses remain for the instrument 50, the controller 21*a* provides the user with a predicted number of uses available.

The controller 21*a* is configured to execute a use prediction algorithm, which may be embodied as software instructions or an application executable by the controller 21*a*. Using the algorithm, the controller 21*a* is configured to predict the total number of uses remaining on the instrument 50 by evaluating the average number of minutes of use for the instrument 50. Thus, if the instrument 50 is used for many short uses, the total number of available uses reported to the user will increase. Conversely, if the instrument 50 is used for many long uses, namely, more minutes per use than for short uses, the total number of available uses is reduced.

The use prediction algorithm provides insight into how many additional uses an instrument likely has remaining based on how the instrument has previously been used. The algorithm is based on the concept that a given instrument 50 has a set total allowed use time before the allowed life of the instrument 50 expires. In another embodiment, the remaining usage life of the instrument 50 may be shown as a percentage, which may be calculated based on the total number of minutes used divided by the total number of minutes allowed for the instrument 50, and showing the user that the instrument 50 is expired once a threshold is reached.

If the instrument 50 is used for a number of short uses, the controller 21*a* displays a larger denominator to the user, indicating that the instrument 50 will last for more discrete uses as compared to the instrument 50 with the same allowed number of minutes that is used in several long uses. The display for the instrument 50 used in several long uses will have a smaller denominator, indicating to the user that the instrument 50 will not be able to be used for as many discrete uses. The total allowed (i.e., maximum) number of uses of the instrument 50 may be adjusted by the user, hospital, or manufacturer.

Furthermore, the use prediction algorithm according to the present disclosure also provides a higher likelihood of the instrument 50 being disabled prior to exceeding the allowed use life. The algorithm utilizes the information gathered about average minutes per use and disables the instrument 50 if the minutes remaining are less than the average minutes per use that the instrument 50 had previously experienced. Disabling the instrument may include any prevention of actuation of the instrument 50, such as stopping the IDU 52 from receiving any user inputs from the surgeon console 30, ignoring user inputs at the surgeon console 30, etc. In addition, disabling the instrument may include preventing an opening/closing of jaws of the instrument, preventing a pivoting or articulation of the jaws or distal end or shaft of the instrument, preventing a rotation of the jaws of the instrument, or any other type of movement of the jaws or shaft of the instrument contemplated by one of skill in the art.

Figure 7:
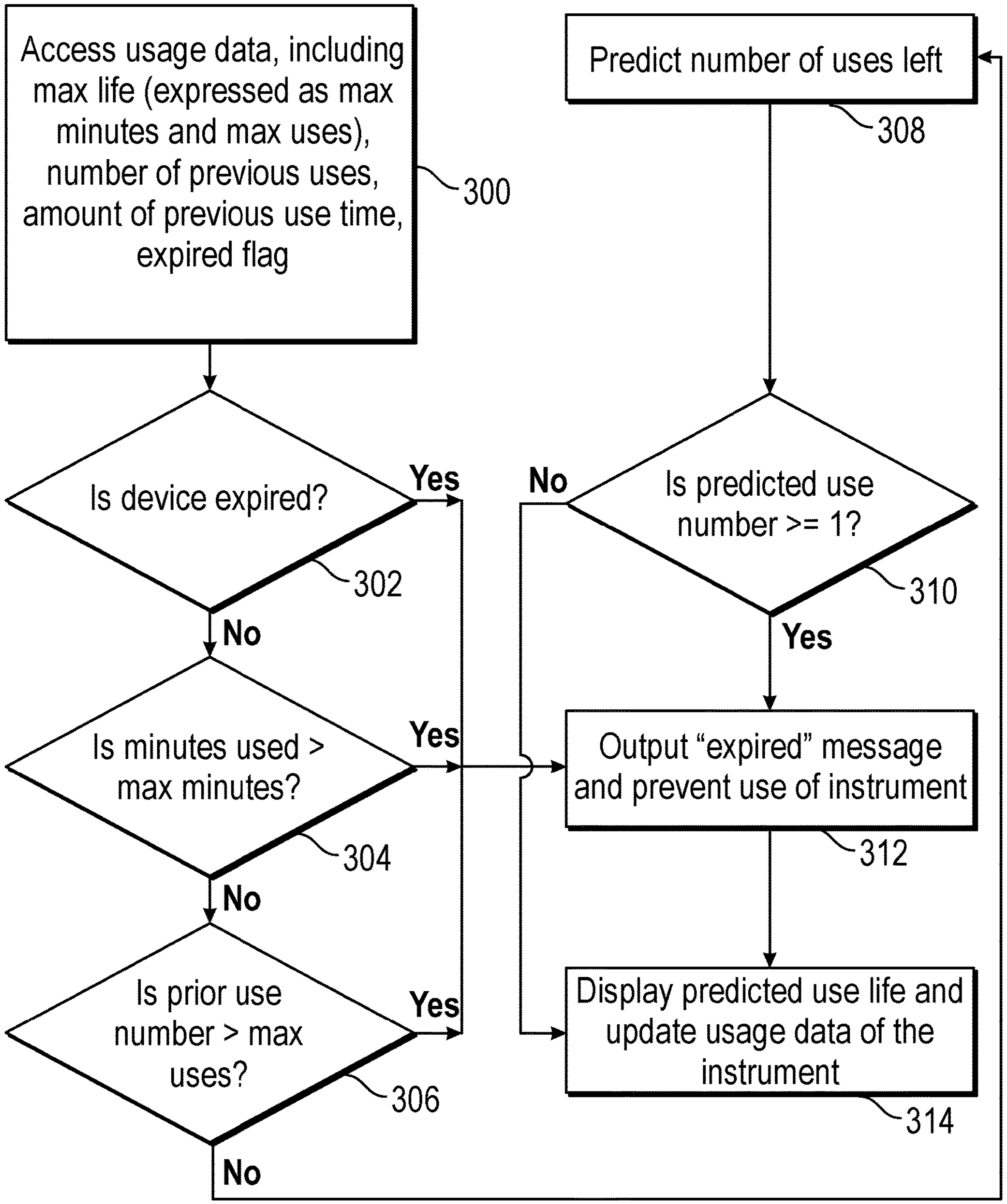
FIG. 7 is a flow chart of a method for instrument use prediction according to the present disclosure.

With reference to FIG. 7, for each instrument 50 that is connected to the robotic arm 40, the controller 21*a* executed the following use prediction algorithm. Initially, at step 300, the usage data from the memory 106 of the instrument 50 is accessed by the controller 21*a*. Usage data includes instrument's maximum (i.e., allowed) life data, which includes maximum uses and maximum time. Use of the instrument 50 may constitute coupling the instrument 50 and activating the drive couplers 102*a-d* by the IDU 52. Thus, once this event occurs, the usage count is incremented by the controller 21*a*. Maximum life values may be preset at the factory for each of the instruments 50.

Usage data may also store previous use data, which includes a number of previous uses, total amount of time of previous uses, and/or an expiration flag, which may be a boolean (i.e., true or false) indicating that the instrument 50 has reached its maximum allowed life.

In embodiments, usage data for each instrument 50 may be stored at another device, such as the control tower 20 and/or a remote server (not shown). Usage data may be stored in a lookup data table and accessed by the controller 21*a* using an identifier associated with the instrument 50. The identifier may be stored in the memory 106 or any other suitable storage means, such as an RFID or a QR code, and the like.

Once the controller 21*a* receives the usage data, the controller 21*a* performs the following verification checks to determine whether the instrument 50 may be used. This includes, at step 302, the controller 21*a* determining if the expiration flag has been set to "true", which may be set after pervious use of the instrument 50, then the controller 21*a* outputs an "expired" message 170 as shown in FIG. 6 at step 312. The message may be an audio and/or visual alarm, button, region, window, a scrolling chevron, and/or any other animation shown on the displays 23, 32, and 34. The controller 21*a* also prevents the surgical robotic system 10 from using the instrument 50. If the expiration flag is "false", the controller 21*a* proceeds to the next verification.

The next verification, at step 304, includes comparing the total number of prior minutes that the instrument 50 was used for is compared to the maximum allowed time. If the previous use time exceeds the maximum allowed time, then the controller 21*a* outputs the "expired" message 170 and disables the instrument 50. Otherwise, the controller 21*a* proceeds to the next verification.

Another verification at step 306 includes comparing the total number of prior uses that the instrument 50 was used for is compared to the maximum allowed number of uses. If the previous use time exceeds the maximum allowed use number, then the controller 21*a* outputs the "expired" message 170 and disables the instrument 50. Otherwise, the controller 21*a* proceeds to the next verification. When a new instrument 50 is installed, the controller 21*a* may output a "new instrument" message 172 stating that this is the first use of the instrument 50.

In addition to the previous verifications, the controller 21*a* also calculates a predicted number of uses remaining at step 308. The prediction includes calculating an average use time by dividing previous use time by previous number of uses. Thereafter, the process includes dividing the maximum allowed time by the average use time to obtain a predicted number of uses. If the predicted number of uses is less than one, then the controller 21*a* outputs the "expired" message 170 and disables the instrument 50. Otherwise, the controller 21*a* outputs a message at step 314 indicating that the instrument 50 may be used and may also output the predicted number of uses remaining as a value.

Predicted use value of the instrument 50 may also be displayed as a ratio 173, as shown in FIG. 6. As described above, the ratio shows "1" as the numerator and the predicted use value as the denominator. The predicted use value may be calculated by dividing the prior use number by the predicted number of uses. In addition, a percentage value and/or a bar graph 174 showing remaining life of the device may be shown. The percentage of life remaining may be calculated based on minutes used divided by the maximum allowed time and converting the ratio into a percentage (e.g., subtracting from 1).

It is envisioned that any of the verifications (i.e., expiration flag, time verification, use verification, predicted use verification) of the use prediction algorithm may be used alone or in any combination, thus, the predicted use verification may be used on its own or in combination with any of the other verifications. Furthermore, the use prediction algorithm may be used for counting surgical instruments or other surgical appliances that are used with surgical systems, such as electrosurgical, ultrasonic, and powered surgical systems.

It will be understood that various modifications may be made to the aspects disclosed herein. In aspects, the color-coded relative position, angular orientation, and operational status of each robotic arm may also be simultaneously viewable on multiple displays. Therefore, the above description should not be construed as limiting, but merely as exemplifications of various aspects. Those skilled in the art will envision other modifications within the scope and spirit of the claims appended thereto.

What is claimed is:

1. A surgical robotic system comprising:

a robotic arm;

a surgical instrument configured to couple to the robotic arm; and a controller configured to:

access usage data pertaining the surgical instrument, wherein the usage data includes a maximum use time, a number of previous uses, and a previous use time;

calculate an average use time by dividing the previous use time by the number of previous uses;

calculate a predicted number of uses remaining for the surgical instrument based on the maximum use time and the average use time; and disable the surgical instrument based on the predicted number of uses remaining in response to the predicted number of uses remaining being less than one.

2. The surgical robotic system according to claim 1, wherein the usage data includes an expired flag.

3. The surgical robotic system according to claim 2, wherein the controller is further configured to disable the surgical instrument based on the expired flag being set to true.

4. The surgical robotic system according to claim 2, wherein the controller is further configured to disable the surgical instrument based on the previous use time exceeding the maximum use time.

5. The surgical robotic system according to claim 2, wherein the controller is further configured to disable the surgical instrument based on the number of previous uses exceeding the number of maximum uses and disabling includes preventing actuation of the surgical instrument in response to user input.

6. The surgical robotic system according to claim 1, further comprising:

a display configured to output a graphical user interface including a usage indicator status pertaining to the surgical instrument.

7. The surgical robotic system according to claim 1, wherein the surgical instrument includes a storage device configured to store the usage data.

8. The surgical robotic system according to claim 1, wherein the controller is further configured to update the usage data following use of the surgical instrument.

9. A method for controlling a surgical system, the method comprising:

accessing usage data pertaining to a surgical instrument, wherein the usage data includes a maximum use time, a number of previous uses, and a previous use time;

calculating an average use time by dividing the previous use time by the number of previous uses;

calculating a predicted number of uses remaining for the surgical instrument, based on the maximum use time and the average use time; and disabling the surgical instrument based on the predicted number of uses remaining in response to the predicted number of uses remaining being less than one, wherein disabling includes preventing actuation of the surgical instrument in response to user input.

10. The method according to claim 9, wherein the usage data includes an expired flag.

11. The method according to claim 9, further comprising:

displaying on a graphical user interface a usage indicator status pertaining to the surgical instrument.

12. The method according to claim 9, updating the usage data following use of the surgical instrument.

* * * * *